United States Patent [19]

Shinoda

[11] 4,141,350
[45] Feb. 27, 1979

[54] VASCULAR SOUND DETECTOR

[75] Inventor: Masayuki Shinoda, Iwakura, Japan

[73] Assignee: Nippon Colin Co., Ltd., Nagaokakyo, Japan

[21] Appl. No.: 722,122

[22] Filed: Sep. 10, 1976

[30] Foreign Application Priority Data

Dec. 3, 1975 [JP] Japan .................. 50-144815
Jun. 19, 1976 [JP] Japan .................. 51-072416

[51] Int. Cl.² .............................................. A61B 5/02
[52] U.S. Cl. ........................... 128/2.05 S; 128/2.05 C
[58] Field of Search ............ 128/2 K, 2.05 A, 2.05 C, 128/2.05 E, 2.05 M, 2.05 P, 2.05 S; 179/1 ST; 181/131, 135, 137

[56] References Cited

U.S. PATENT DOCUMENTS

| | | | |
|---|---|---|---|
| 910,854 | 1/1909 | Pilling | 128/2 K |
| 2,271,467 | 1/1942 | Smithline | 181/131 |
| 2,699,465 | 1/1955 | Hamilton | 179/1 ST |
| 3,076,870 | 2/1963 | Jones, Jr. | 179/1 ST |
| 3,148,677 | 9/1964 | Smith | 128/2.05 S |
| 3,348,534 | 10/1967 | Marx et al. | 128/2.05 M |
| 3,525,810 | 12/1966 | Adler | 128/2.05 S |
| 3,633,703 | 1/1972 | Littman | 128/2.05 S |
| 3,742,937 | 7/1973 | Manvel et al. | 128/2.05 E |

FOREIGN PATENT DOCUMENTS 1084208  3/1956  France ........................ 128/2.05 A Primary Examiner—Robert W. Michell
Assistant Examiner—Francis J. Jaworski
Attorney, Agent, or Firm—Browdy and Neimark

[57] ABSTRACT

Blood vessel or vascular sound collecting device (hereinafter simply referred to as sound detector) insertable in a manschette or cuff for collecting the blood vessel sound and supplying the data to an automatic sphygmomanometer, having a hollow unitary space of substantially rectangular shape in plan view, enveloped by a flexible inner side wall of substantially rectangular shape in plan view, and a rather thicker and less flexible outer side shell of substantially rectangular shape in plan view, with an elongated rib integrally formed therewith for preventing the hollow space from being squashed, and a highly sensitive microphone exposed in the hollow space for sound collecting, which sound detector has a fine aperture with diameter to prevent same from picking up noises and being affected by the fluctuation of internal air pressure.

4 Claims, 11 Drawing Figures

VASCULAR SOUND DETECTOR

BACKGROUND OF THE INVENTION

The present invention relates to a sound detector or sound collecting device for detecting blood vessel sounds or vascular sounds by means of a microphone to automatically measure the blood pressure, more particularly, to an improved and unique sound detector to be insertable in a manschette, for use in an automatic sphygmomanometer, provided with a hollow space enveloped by a flexible filmy inner side wall and a rather flexible but less thin outer side shell having an elongated rib integrally formed therewith and a highly sensitive condenser microphone housed in a case connected to the hollow space through a passage for outputting sounds. The present invention has further greatly contributed to the art of this line by providing a few novel modifications such as an arcuate form sound detector for better adaptation on the human body and disposing of a fine aperture in the hollow space for conspicuously reducing the noise collection while measuring.

A blood pressure measuring method by pumping pressurized air into a manschette (an elongated belt like air bag wound on an upper arm of a patient) to raise the air pressure to a certain value once and then gradually lowering it for palpating or ausculating the pulsation at an artery was popular in the past. In recent years a blood measuring device (called an automatic sphygmomanometer), wherein systolic and diastolic pressure are electrically measured (an average blood pressure or pulsation is also measured, if necessary) and digitally indicated by means of vascular sound detection with a microphone, has been developed and put in practice. This sphygmomanometer has largely improved the blood pressure measuring as regards an elimination of individual differences depending on the examiner's skill and a reduction of measuring errors; it still can not be said, however, to be free of some disadvantages. In this conventional instrument a sound detecting method by directly contacting the sound detector including a ceramic microphone or dynamic microphone on a body portion of a patient relatively close to an artery has been generally adopted. Principal inconveniences accompanied thereby are numerated as follows: it has to be properly placed in close contact with the human body (e.g. over an artery of the upper arm), but because it is housed in a substantially flat metalic case (20–25mm in diameter) placement as often difficult in close contact to a human body especially for thin or slender patients or infants; and microphones of this sort are changeable in output level in a low frequency band less than 100 Hz as can be seen in FIG. 2.

A primary object of this invention is to provide a novel sound detector for eliminating the disadvantages inevitable in conventional instruments. The gist of this invention resides in that the sound detector has a hollow unitary space, rather flexible as a whole, having a longitudinal rib disposed therein to maintain the hollow space as it is regardless of some outer pressure, and that it is provided with a highly sensitive condenser microphone housed in a case with the sound collecting portion thereof being disposed to the hollow space.

Another important object of this invention is to provide a novel sound detector to be insertable in the manschette of an automatic sphygmomanometer, wherein the hollow unitary space is of a concave shell for still easier contact on the human body, with the inside surface being made of a thin flexible film and the outside surface being made of a thicker and rather rigid material, and the unitary hollow space is communicated with the outside atmosphere through a fine aperture for greatly reducing the disturbing noise simultaneously picked up.

SUMMARY OF THE INVENTION

A blood vessel sound detector for insertion into a manschette of an automatic sphygmomanometer to efficiently measure vascular sounds without being disturbed by unnecessary noises is the gist of the present invention. For that purpose the present invention provides a novel instrument having (a) a hollow unitary space enveloped by a flexible filmy inner side wall and a fairly flexible but thicker outer side shell made of soft materials with an elongated rib to avoid the hollow space being squashed; (b) a highly sensitive microphone, a condenser microphone for sound collecting exposed in the hollow space; (c) a general contour of arcuate form, in some embodiments, for better adaptation to the human body; and (d) a fine aperture, in some embodiments, disposed in the hollow space body for preventing noises from being collected by means equalizing the air pressure inside thereof and the atmosphere.

DETAILED DESCRIPTION OF THE INVENTION

For other objects and for a better understanding of the invention, reference may be had to the following detailed description taken in conjunction with the accompanying drawing, in which.

Figure 3:
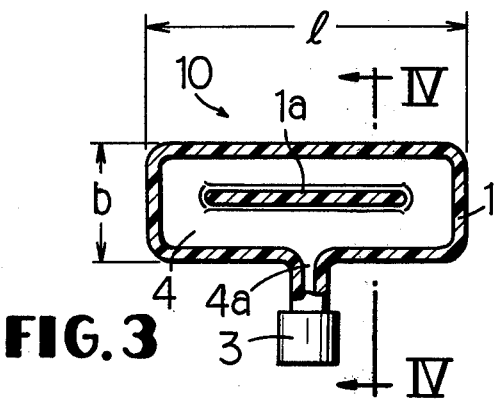
FIG. 3 is a cross sectional view of a sound detector of a first embodiment in accordance with this invention taken along the line III — III of FIG. 4.
Figure 4:
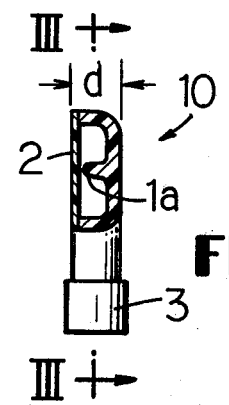
FIG. 4 is a transverse sectional view of the same embodiment taken along the line IV — IV of FIG. 3.

In a first embodiment, shown in FIG. 3 a horizontal section thereof and FIG. 4 a transverse section, a sound detector generally designated at 10 is approximately 80mm in length l, 30mm in width b, and 8mm in depth d, and is composed of an inner side filmy wall 2 of 0.5–1.0mm of thickness and an outer side shell 1 of 2.0–3.0mm thickness, having an integrally formed longitudinal rib 1a therein. Both of these inner side wall 2 and outer side shell 1 are made of neoprene (JIS 60–80 degrees hardness), the former being rather thin for the purpose of facilitating detection of vascular sound and the latter being thicker for preventing outside noises from coming in. A microphone 3 employed herein is housed in a cylinder of a size, for example, 10mm in diameter and 10mm in length, which is in communication with the hollow space 4 through passage 4a, the hollow space 4 being enveloped by the inner side wall 2 and the outer side shell 1.

Figure 5:
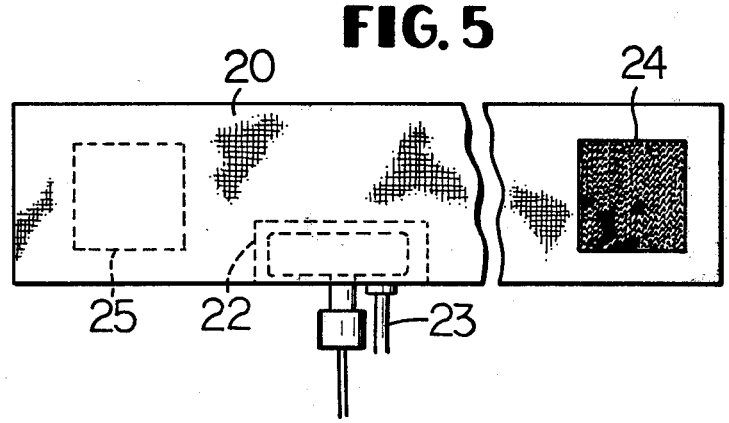
FIG. 5 is a plan view of a manschette in which the sound detector shown in FIG. 3 is inserted.

The sound detector 10 is usually inserted in a pocket 22 of a manschette 20 in the known way shown in FIG. 5. The manschette 20 is fairly tightly wound on an upper arm of a patient and fixed with a freely engageable fastener (for example with a "magic fastener"), into an air bag thereof being pumped with pressurized air through a pipe 23 from an air supplying means which is installed in an automatic sphygmomanometer (not shown). After the air pressure has been raised as high as to restrain the pulsation of artery, the air is released to gradually lower the air pressure for allowing the restart of vascular sound. The blood pressure at this moment is a systolic pressure or a maximum blood pressure. A further lowering of the air pressure will cause the vascular sound to grow larger, noisy, clear, and then suddenly feeble and finally inaudible. The blood pressure when the vascular sound suddenly becomes feeble or inaudible, as is well-known, is a diastolic or minimum one.

Automatic sphygmomanometers attempt to detect these vascular sounds with a microphone 3 and to digitally, for example, indicate the systolic and diastolic pressure values by electronically treating the data within the main body thereof.

Figure 1:
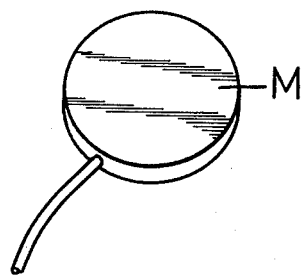
FIG. 1 is a perspective view of a conventional microphone means.
Figure 2:
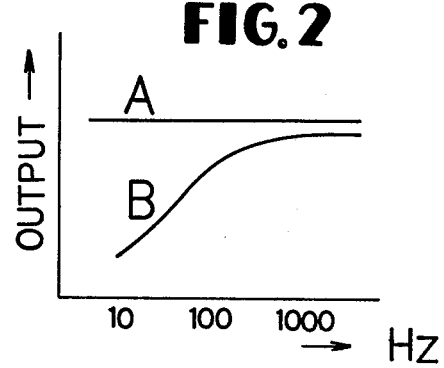
FIG. 2 is a graph for making a comparison of features between the conventional microphone (B) and that of the present invention (A) (frequency vs. output)

What improvements the present invention has achieved will be described below. (a) A flexible structure as a whole of the sound detector 10 permits the same to be fairly tightly contacted against the human body (specifically on an upper arm) together with the manschette, having precluded the disadvantages of the conventional instruments such as a poor contactability on an application place or a limitation of the application place right above the artery. (b) Existence of the hollow unitary space 4 with a large width renders usage of the newly invented instrument quite easy and convenient, because it may cross the artery at any portion thereof for detecting the vascular sound. It has emancipated the cumbersome selection of application place. (c) Selection of the condenser microphone 3 has largely enhanced the sensitivity of the sound detector 10, which microphone is relatively unchangeable in output even in the low frequency band (FIG. 2, A). Considering the following fact, merits of replacing the conventional dynamic or ceramic microphone with the condenser microphone can not be exaggerated: (1) Korotkoff sounds which are closely related with the systolic and diastolic pressure generally belong to 40-80 Hz; (2) normal pulsation sounds are below 40 Hz.

Figure 6:
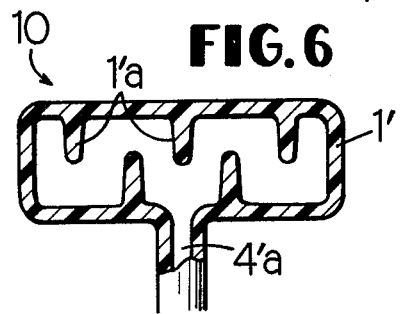
FIGS. 6 and 7 are a cross sectional view corresponding to FIG. 3 of a second and a third embodiment, respectively.
Figure 7:
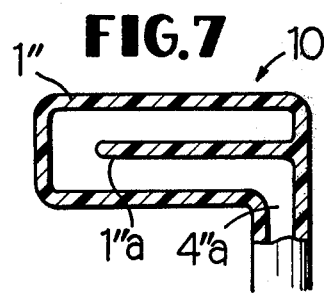

A second embodiment shown in FIG. 6 and a third embodiment shown in FIG. 7 are all modifications of the first embodiment with regards to the shape and position of the rib 1a within the hollow space of the sound detector 10, with the substance and the thickness of the inner side wall 2 and the outer side shell 1 being similar to the first embodiment. The second embodiment is characterized in that the same is superior in flexibility and contactability on the upper arm because of replacement of the longitudinal rib 1a with a plurality of lateral ribs 1'a. The third embodiment having a passage 4"a, between the hollow space 4 and the microphone 3, connected at one end of the hollow space 4 is suitable when there is a necessity of setting aside the sound output passage to the end.

Figure 8:
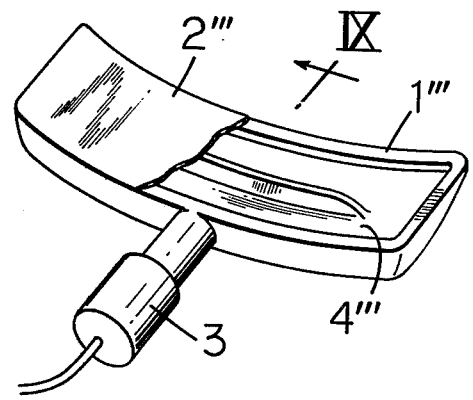
FIG. 8 is a perspective view, partly broken away, of a sound detector of a fourth embodiment.
Figure 9:
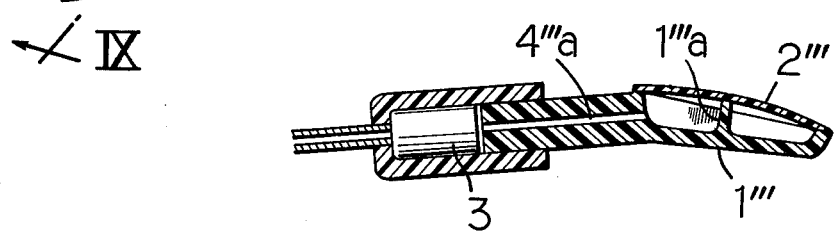
FIG. 9 is a cross sectional view taken along the line IX — IX of FIG. 8.

A fourth embodiment is, in fact, still another modification; unlike the aforementioned embodiments, this one is as shown in FIGS. 8 and 9 concave in the inner surface, and consequently the general view thereof is curved toward the inside. The inner side wall 2''' is preferably a flexible film made of neoprene with the thickness of 0.3-1.0mm; the outer side shell 1''' is preferably made of relatively soft resin or rubber; the unitary hollow space 4''' is connected to the housing for the microphone 3''' through a passage 4'''a; in the hollow space 4''' is disposed a longitudinal rib 1'''a integrally formed of the shell 1'''. This embodiment, which is different from the later described fifth embodiment only in one aspect, has achieved a significant improvement in the practical use of this instrument because of the general contour of curved structure and the more flexible substance used in the body for better adaptation on the human upper arm.

Figure 10:
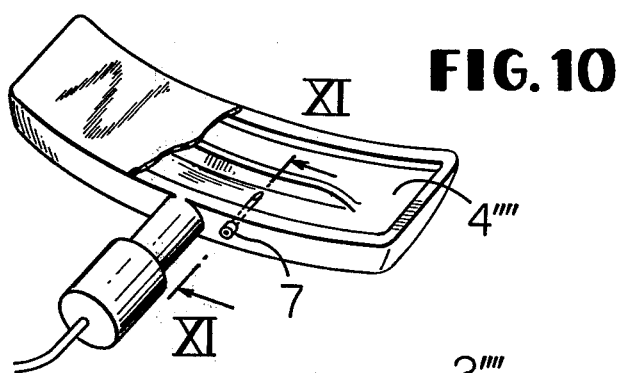
FIG. 10 is a perspective view, partly broken away, of a sound detector of a fifth embodiment.
Figure 11:
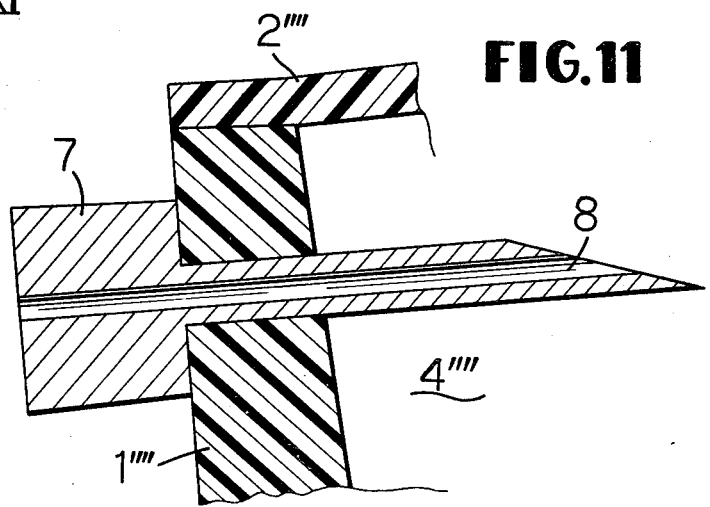
FIG. 11 is a cross sectional view taken along the line XI — XI of FIG. 10.

A fifth embodiment, shown in FIGS. 10 and 11, is the last but the most important modification and needs to be described in greater detail. The greatest feature of this embodiment lies in a unique idea of disposing the later described fine aperture communicating the hollow space 4'''' with the outside atmosphere. In addition to the abovementioned greatly improved contactability of this instrument on the human body, immeasurable merits that the simple idea of disposing a fine aperture in the hollow space has brought about must be emphasized.

As shown in FIGS. 10 and 11 clearly, an injection needle 7 having a fine hole 8 with an inner diameter of 0.6mm is pierced through the shell 1'''' for communicating the hollow space 4'''' with the atmosphere; the communicating means is not limited to the injection needle but a usual fine metal pipe or a mere tiny hole may be permissible; the position of the communication aperture is not limited to the shown one in the Figure, either; the diameter of the aperture shall be, however, in a limited range.

The disposing of this fine aperture has resolved three big problems, i.e., the elimination of disturbing noises traditionally inevitable to this kind of instrument; elimination of errors in measurements; and elimination of changeability of microphone sensitivity. A perfect air tightness in the hollow space readily changes the pressure therein depending on the degree of pressing the manschette, which consequently leads to the change of sensitivity of the sound detector. The fine aperture which makes the pressure inside equal to that outside has eliminated the above complaint. In the air tight type instrument the microphone is liable to collect noises from muscular friction and other sources together with the vascular sounds and to disturb the correct measurement. This type of noises can not be fully eliminated even by an improvement of the electrical circuit of the sphygmomanometer. The simple fine aperture in this embodiment has been successful in the preclusion of noises being collected.

For the purpose of equalizing the air pressure inside and that outside there can be no strict limitation as regards the inner diameter of the aperture provided that it be more than a minimum limit; for the purpose of preventing the noise from being collected, however, the inner diameter thereof should be of a limited scope. If it is too small the noise preventing effect can not be expected, and if it is too large the sound collecting effect is likewise degraded. For expecting the essential effect of this invention the sound detector should be sensitive enough for the frequency band 5-200 Hz and insensitive for the noises belong to the higher frequency band than that.

The inner diameter of the fine aperture might depend upon the shape of the hollow space 4, material feature, thickness, etc., of the flexible filmy inner side wall; the experimental data by means of an injection needle based on the body of the sound detector having the size of 90 × 20 × 4mm, with a concave inner side wall of neoprene 0.5mm thickness, show:

an aperture with the inner diameter from 0.2mm to 1.5mm is effective; and especially in the range of 0.5mm–1.5mm best results are obtainable.

It will be obvious to those skilled in the art that various changes may be made without departing from the scope of the invention and the invention is not to be considered limited to what is shown in the drawing and described in the specification.

What is claimed is:

1. A vascular sound detector for insertion into a blood pressure measuring manchette, comprising a fairly flexible thin filmy wall having a thickness of between 0.3mm and 1.0mm and being made of Neoprene having a hardness of between JIS60 and JIS80 degrees, a relatively thick outer side shell of soft resilient deformable material having a peripheral outer wall of substantially rectangular shape connected to said filmy wall to define therebetween a hollow substantially rectangular space of constant depth and defining an enclosure which is flexible as a whole, at least one longitudinal straight elongated internal rib integrally formed on an intermediate portion of said outer side shell, with its ends spaced from said rectangular outer wall, for sustaining said hollow space without inhibiting longitudinal air movement therein, a condenser microphone communicatively connected to said hollow space, and means to reduce the pickup of extraneous noise without adversely affecting sound collecting, as well as to decompose a vascular sound distinctively according to different frequencies, said means comprising an element having a passage with a diameter between 0.2mm and 1.5mm extending to said hollow space and connecting said hollow space with the ambient atmosphere, whereby said hollow space is maintained as a unitary space and the sound sensing portion of said microphone is directly exposed to the inside of said hollow space.

2. A vascular sound detector as set forth in claim 1, wherein a plurality of rather short spaced internal ribs integrally formed with said outer side shell are disposed across said hollow space.

3. A vascular sound detector as set forth in claim 1, wherein a said internal elongated rib integrally formed with said outer side shell projects longitudinally from an end of said shell across said hollow space, and a sound output passage leading to said microphone is disposed near said end from which said rib projects.

4. A vascular sound detector as set forth in claim 1, wherein said hollow space is generally of arcuate shape enveloped by a concave inner side wall and a likewise arcuate outer side shell for best adaptation on the human body.

* * * * *